United States Patent [19]

Johnson

[11] Patent Number: 5,049,744
[45] Date of Patent: Sep. 17, 1991

[54] RADIOACTIVE PARTICLE DENSITOMETER APPARATUS EMPLOYING MODULATION CIRCUITRY

[75] Inventor: Herbert A. Johnson, Walnut, Calif.

[73] Assignee: The United States of America as represented by the Secretary of the Navy, Washington, D.C.

[21] Appl. No.: 461,898

[22] Filed: Jan. 8, 1990

[51] Int. Cl.⁵ .................. G01N 23/06; G01N 9/24
[52] U.S. Cl. .................. 250/308; 250/358.1; 250/370.02
[58] Field of Search .................. 250/308, 364, 370.02, 250/380, 390.06, 358.1

[56] References Cited

U.S. PATENT DOCUMENTS

| | | | |
|---|---|---|---|
| 3,196,271 | 7/1965 | Wright | 250/308 |
| 3,783,292 | 1/1974 | Alter et al. | 250/83 |
| 3,899,878 | 8/1975 | Compton et al. | 250/308 |
| 4,172,225 | 10/1979 | Woldseth et al. | 250/306 |
| 4,262,203 | 4/1981 | Overhoff | 250/374 |
| 4,328,610 | 5/1982 | Thompson et al. | 29/571 |
| 4,527,064 | 7/1985 | Anderson | 250/374 |
| 4,584,161 | 4/1986 | Post et al. | 376/143 |
| 4,607,165 | 8/1986 | Burghoffer et al. | 250/435 |
| 4,614,870 | 9/1986 | Morrison | 250/358.1 |

*Primary Examiner*—Edward P. Westin
*Assistant Examiner*—Drew A. Dunn
*Attorney, Agent, or Firm*—Thomas E. McDonnell; Edward F. Miles

[57] ABSTRACT

An apparatus and method for measuring the density of a low density medium such as air by measuring the absorption of radioactivity decay particles such as alpha particles in the air. The apparatus includes a source of alpha particles from which the alpha particles are directed to the air sample to be measured. An alpha particle detector is spaced from the source by a path distance which traverses the air sample. The detector is located at an operating point which corresponds to the path distance where one half of the emitted alpha particles are detected. A control system employs a double sideband, suppressed carrier waveform generator which supplies a double sideband, suppressed carrier as a reference signal and supplies a double sideband, suppressed carrier waveform that is modulated by the detection signal. A difference signal between the reference signal and the modulated detection signal is used to operate a feedback controlled servomechanism that moves the source of alpha particles toward or away from the detector depending upon the density of the medium. Distances moved by the alpha particles source are related to the density of the medium.

16 Claims, 4 Drawing Sheets

TIME

RADIOACTIVE PARTICLE DENSITOMETER APPARATUS EMPLOYING MODULATION CIRCUITRY

BACKGROUND OF THE INVENTION

The present invention described herein relates to the field of density measurement. More specifically, the invention relates to devices and techniques using radioactive decay to measure density. The invention especially relates to alpha particle densitometers.

Frequently, the density of very thin materials or gases, such as air, must be measured automatically to a high degree of accuracy. This requirement is particularly desired in an airborne vehicle for which a measurement of air density is employed for the calculation of air pressure. Radioactive particles may be employed to determine air density since particles from a particular radioactive source have a discrete energy and a predictable distance of decay from the source in a medium of a particular density such as air.

A radioactive source has a specific half-life whereby the source is constantly undergoing decay. Since a particular radioactive substance that emits alpha particles is constantly decaying with time, the number of alpha particles which are emitted varies as a function of time thus requiring calibration of the emission of alpha particles at appropriate time intervals in order to measure density accurately. Thus, it would be desirable to provide an alpha particle densitometer that compensates for the fact that the alpha particle source undergoes constant decay.

Still other radioactivity-based methods for measuring the density of low density materials, such as air, require calibration at periodic intervals. Similarly, it would be desirable, in general, to provide a radioactivity-based densitometer that does not require periodic calibrations due to the decay of the radioactive substance and that compensates for that decay.

Other radioactivity-based methods for measuring the density of air use beta particles, and these methods are not very accurate. It would be desirable to have a very accurate method for measuring air density.

SUMMARY OF THE INVENTION

Accordingly, it is an object of the present invention to provide an alpha particle densitometer that compensates for the fact that the alpha particle source undergoes constant decay.

Another object of the invention is to provide a radioactivity-based densitometer that does not require periodic calibrations due to the decay of the radioactive substance.

Still another object of the invention is to provide a very accurate method for measuring the density of air and other low density materials.

Briefly, these and other objects are accomplished by the invention relating to an apparatus and method for measuring a characteristic (e.g. density) of a medium (e.g. air) by measuring absorption of radioactivity decay particles (e.g. alpha particles) in the medium. The apparatus is comprised of: a source providing radioactivity decay particles at a source emission rate for providing radioactivity decay particles to the medium; a radioactivity detector separated from the source by a path distance which traverses a portion of the medium, for detecting radioactivity decay particles emitted from the source which traverse the portion of the medium, wherein the detector provides a detection signal representing a detection rate; and means, responding to the detection signal, for varying the path distance for maintaining the detection rate in a narrow range of variation from a predetermined fraction of the source emission rate, whereby variation of the path distance is indicative of variation in a characteristic of the medium. By maintaining the detection rate in a narrow range of variation of a predetermined fraction of the source emission rate, periodic calibration to compensate for changing rates of decay of the source, as time progresses, is unnecessary. In effect, the apparatus of the invention is self-calibrated.

More specifically, the detector detects radioactive particles that have traversed the medium. If, after a period of time, the detector detects a lower count of radioactive particles than at an earlier time, the detector itself is incapable of indicating the cause of the decrease in radioactive particles. More specifically, the count of radioactive particles can decrease either because the medium changes to a greater density, or because the rate of emission of the radioactive particles from the source has decreased. With the present invention, a radioactive particle densitometer is provided that is accurate with respect to changes in the medium and is automatically self calibrated with respect to changes in decay of the radioactive source.

In an apparatus employing alpha particles for determining the density of a low density medium, preferably the path distance terminates at an operating point which, within a narrow range of variations, corresponds to the distance at which the detected rate of alpha particles that have passed through the medium drops rapidly to a predetermined fraction of approximately one half the rate of alpha particle emission at the alpha particle source. This path distance is called the mean range. Whether the source count rate is high or whether the source count rate is low, for a given medium, the distance of the mean range from the source remains the same.

However, for a given radioactive source, if the character of the medium changes, e.g. the density changes, then the mean range would change in response to changes in the medium. Since the mean range does not change due to a decaying radioactivity source, the change in the mean range is entirely due to changes in the character of the medium. More specifically, for an initialized device with an initial mean range based on a given source decay and based on an initially measured medium, with the invention, a change in the mean range would be due to a change in the medium. In this way, changes in the mean range can be correlated with respect to changes in the medium.

Preferably, a double sideband, suppressed carrier is used to provide a signal for driving a feedback controlled servomechanism for varying the path distance to follow the operating point, within a narrow range of variation, for any change in the medium. More specifically, a double sideband, suppressed carrier signal is modulated by oscillations of an alpha particle source within a narrow range of variation about the operating point. As the alpha particle source decays over time, the apparatus of the invention maintains the path distance of the alpha particle source from the detector to coincide with the mean range which terminates at the operating point.

If there were no changes in the medium, the mean range would be constant; that is, the radioactive source would dither over a narrow range so that the terminal end of the path distance would dither over a narrow range around the operating point. However, when the character of the medium does change, the path distance (mean range) also changes, and the operating point shifts to coincide with the shift in the path distance. The shift of the path distance and operating point beyond the narrow range of dithering is due only to the change in the character of the medium. There is no component of the path distance shift due to the inevitable change in the rate of decay of the radioactive source.

More specifically, the means for varying the path distance include a feedback controlled servomechanism controlled by a demodulated difference signal which represents a difference between (a) a reference signal of a double sideband, suppressed carrier where the reference signal represents the predetermined fraction of the rate of alpha particles emitted from the source at the operating point, and (b) a detection signal modulating the double sideband, suppressed carrier where the detection signal represents the detected rate of alpha particles passing through the path distance, whereby density changes in the medium are related to the difference signal.

Other objects, advantages and novel features of the invention will become apparent from the following detailed description of the invention when considered in conjunction with the accompanying drawings herein.

DESCRIPTION OF THE PREFERRED EMBODIMENT(S)

Figure 1:
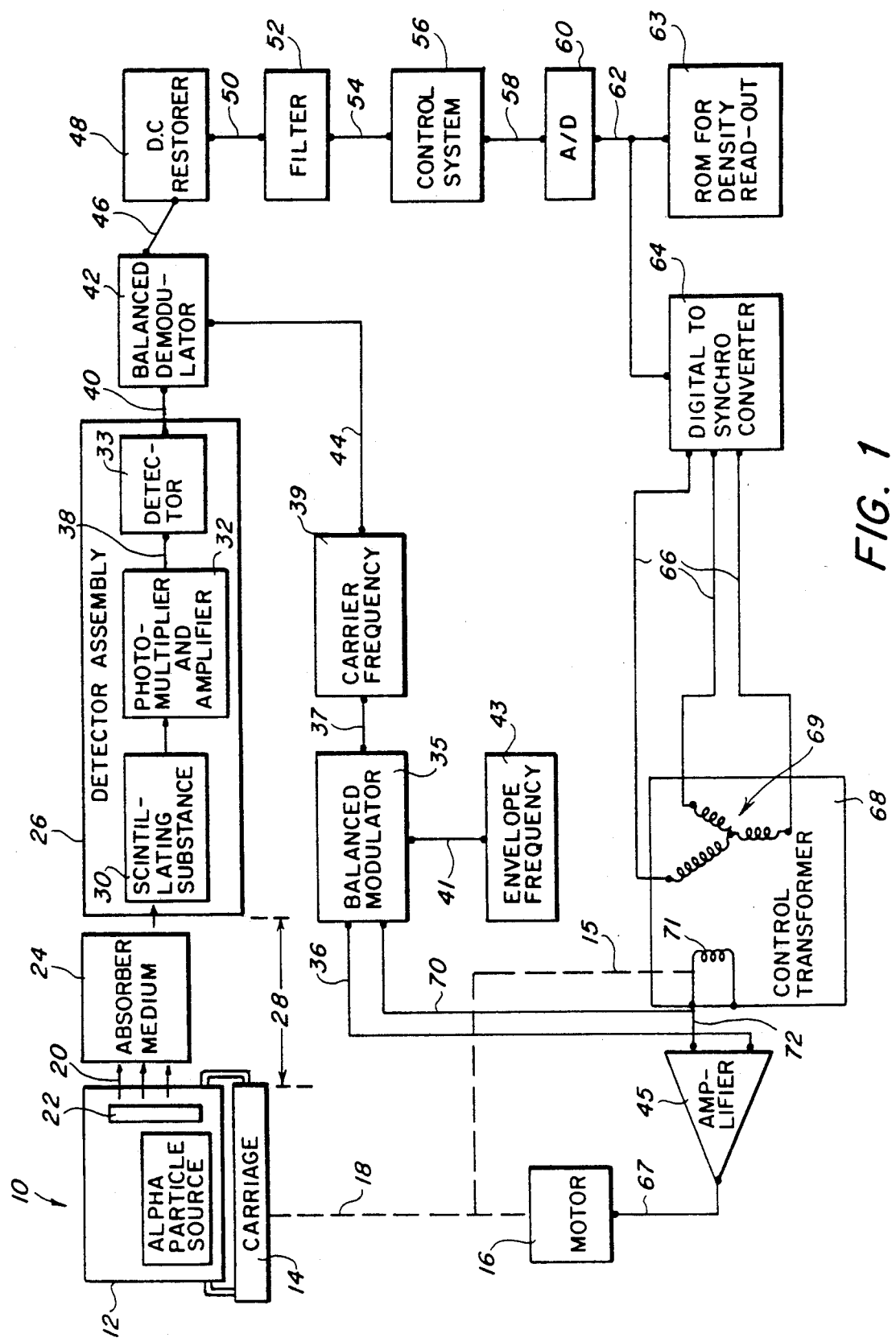
FIG. 1 is a schematic diagram of one embodiment of the invention employing an alpha particle source, a detector employing a scintillating substance, a double sideband, suppressed carrier signal, and a servo-motor for varying the path distance.

With reference to FIG. 1, an alpha particle densitometer system 10 in accordance with the invention is depicted. An alpha particle source assembly 12 is provided. The source assembly 12 includes a source based on polonium-210 which is a good source of alpha particles and decays into lead-206. The half-life of polonium-210 is 138 days. (Polonium 210 is given as an example; any other appropriate radioactive source could be employed also.) The alpha particle source assembly 12 is supported by a movable carriage 14 that is capable of being moved by motor 16 through shaft 18.

The alpha particle source assembly 12 has a collimator 22 which provides a collimated beam 20 which passes through a medium 24 to a detector assembly 26. A path distance 28 (also the mean range) is defined as the distance from the source assembly 12 to the detector assembly 26 through the medium 24. The medium 24 in FIG. 1 is simply ambient air.

The detector assembly 26 includes a scintillating substance 30 that scintillates providing light pulses when exposed to alpha particles, a photomultiplier and amplifier 32 which detects the scintillations and modulates a double sideband, suppressed carrier with electrical pulses representing the scintillation light pulses, and a detector 33 which filters out the electrical pulses and provides a double sideband suppressed carrier modulated by the pulses and provides an electrical output signal representative of the detected alpha particles. The scintillation-pulse-modulated output signal from the detector assembly 26, on line 40 as explained below, is employed ultimately for controlling the motor 16 for moving the carriage 14.

The motor 16, shaft 18, carriage 14, and means for controlling the motor 16 operate as a servomechanism for moving the source 12 toward or away from the detector assembly 26 to alter the path distance 28. The path distance 28 is decreased when the density of the medium increases; and the path distance 28 is increased when the density of the medium decreases.

Figure 2:
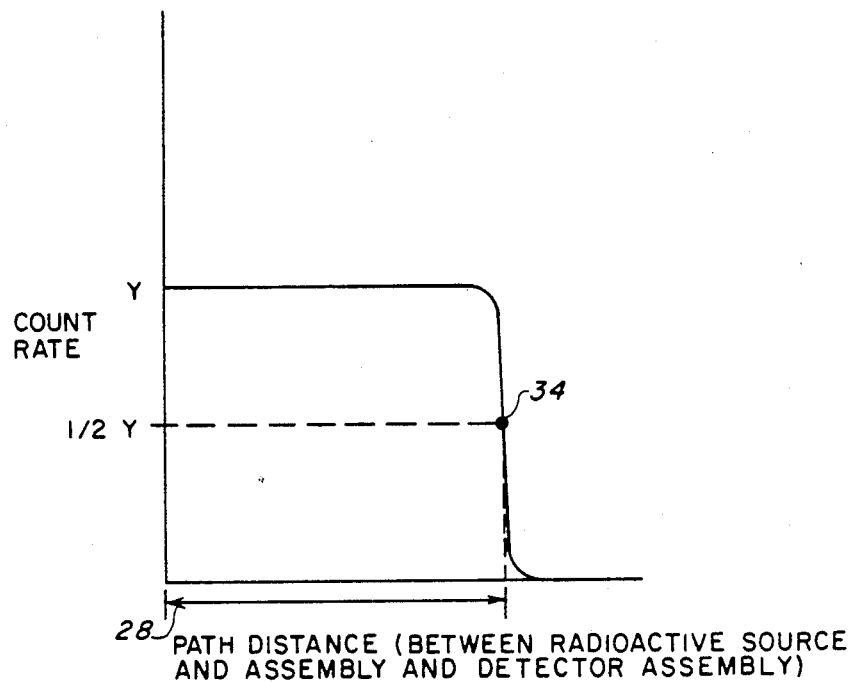
FIG. 2 is a curve showing the relationship of the detected alpha particle count rate for a given medium versus the distance of the detector from the source, wherein the operating point is in the region of rapidly falling off detected count rate.

Referring to FIG. 2, a curve is shown which depicts the relationship between the alpha particle count rate that is detected by the detector assembly 26 versus the path distance 28 between the alpha particle source assembly 12 and the detector assembly 26. It is noted that, for a given medium, the count rate has the relatively constant value "Y" for a substantial part of the path distance 28. However, when the alpha particle source assembly 12 is moved away from the detector assembly 26 so that the path distance 28 nearly equals the path distance of the operating point 34, within a narrow range the detected count rate falls off dramatically near the operating point 34. For convenience, the operating point is located at one end of the path distance 28 and is the point at which the detected count rate is one half (Y/2) of the count rate at the alpha particle source assembly 12. This path distance, as mentioned above, is also called the mean range, and the mean range for alpha particles at sea level is approximately 3.8 cm.

In initializing the system of the invention, the alpha particle source 12 would first be placed near the detector assembly 26. As the alpha particle source 12 is moved away from the detector assembly 26, readings would be taken of the alpha particle count rate. Once the measured alpha particle count rate is one-half of the count rate at the alpha particle source 12, movement of the alpha particle source 12 is stopped. Then, the other system components, particularly amplifier 45, are initialized so that the alpha particle count rate is automatically maintained by the system within a narrow range encompassing one-half the source count rate; that is, the alpha particle count rate of one-half the source count rate becomes the operating point for the system to maintain and about which the system dithers.

As long as the detected count rate is within a narrow range encompassing one-half of the source count rate, the system is said to be in balance. When the detected count rate is either greater than or less than the narrow range encompassing the source count rate, the system is said to be out of balance. Once the system is out of balance, the system automatically places itself back in balance by moving the alpha particle source 12 either closer to or farther away from the detector assembly 26 as appropriate.

More specifically, when the density of the medium increases, and the detected count rate decreases as a result, the system automatically moves the alpha particle source 12 closer to the detector assembly 26, the distance moved representing the increase in density of the medium and the total path distance representing the density of the medium. When the alpha particle source 12 gets sufficiently close to the detector assembly 26, the detected count rate is increased sufficiently, and the system enters into a balanced condition once again. Conversely, when the density of the medium decreases, and the detected count rate increases as a result, the system automatically moves the alpha particle source 12 farther away from the detector assembly 26, the distance moved representing the decrease in density of the medium. When the alpha particle source 12 gets sufficiently far away from the detector assembly 26, the detected count rate is decreased sufficiently, and the system enters into a balanced condition once again.

More specifically, the system is designed to cause the alpha particle source 12 to automatically dither, that is oscillate back and forth across the operating point within a narrow range of distance. By constantly dithering about the operating point, the system is very responsive to slight changes in the operating point due to density changes in the medium.

In accordance with the invention, maintenance of the source assembly 12 with respect to the detector assembly 26 so that one end of the path distance 28 coincides with the operating point 34 is based upon the use of modulation and demodulation techniques for a double sideband, suppressed carrier.

Figure 3:
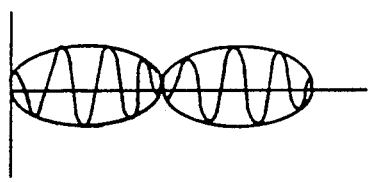
FIGS. 3-11 are depictions of waveforms detected at specific points in the embodiment shown in FIG. 1.

Referring again to FIG. 1, and also to FIGS. 3–11 as described below, line 36 carries balanced a/double sideband, suppressed carrier signal, as shown in FIG. 3. The balanced double sideband, suppressed carrier signal is produced in balanced modulator 35 which receives a carrier frequency on line 37 from a carrier frequency generator 39 and receives an envelope frequency on line 41 from an envelope frequency generator 43. The waveform on line 36 serves as a double sideband, suppressed carrier reference signal and is fed to amplifier 45. Similarly, a reference signal is on line 70. The reference signals on lines 36 and 70, are compared with a signal ultimately derived from the alpha particle detector signal on line 40 to provide a signal which is used, by operating through a servomechanism explained further below, for moving the alpha particle source assembly 12 so as to maintain the path distance 28 equal to the distance between the source assembly 12 and the operating point graphically depicted as point 34 on the curve shown in FIG. 2.

The double sideband, suppressed carrier signal fed to amplifier 45 is used to drive motor 16, carriage 14, and alpha particle source 12 in accordance with the double sideband, suppressed carrier whether or not a difference signal is present on line 67, whereby the alpha particle source 12 dithers around the operating point 34 (in FIG. 2) whether or not a difference signal is present on line 67.

Figure 4:
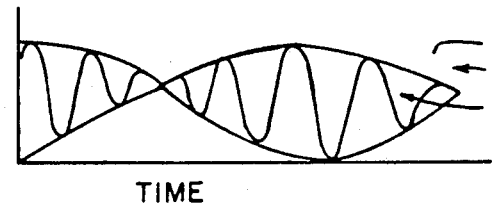

As the alpha particle source 12 is driven to dither with respect to the operating point 34 by the double sideband, suppressed carrier, the emitted alpha particles from the alpha particle source 12 modulate the double sideband, suppressed carrier as shown in FIG. 4. The type of modulation on the double sideband, suppressed carrier is one of two types: either modulation representing the alpha particle source 12 in balance with respect to the operating point 34 (shown in FIG. 5 with the emission pulses having been filtered out on line 40) or modulation representing the alpha particle source 12 out of balance with respect to the operation point 34 (shown in FIG. 6 with the emission pulses having been filtered out on line 40).

Figure 7:
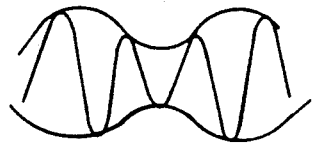

When the modulation from the alpha particle source 12 is in balance, no error signal is developed between the double sideband, suppressed carrier signals; and the path distance 28 is not changed. A demodulated, in balance waveform is shown in FIG. 7 and is present in a balanced demodulator 42. A demodulated, out of balance waveform is shown in FIG. 7 and is alternatively present in the balanced demodulator 42.

When the modulation signal from the alpha particle source 12 is out of balance with respect to the double sideband, suppressed carrier signal, a positive or negative error signal is developed which controls the servomechanism to shift the alpha particle source 12 to provide either a positively altered or negatively altered path distance 28. The altered path distance 28 is correlated to an altered density measurement of the medium.

On the other hand, when the modulation signal from the alpha particle source 12 is in balance with respect to the double sideband, suppressed carrier signal, a zero error signal is developed, and the servomechanism is not caused to shift the alpha particle source 12.

On line 38, the modulated waveform mentioned above and shown in FIG. 4 is present. This is the output of the photomultiplier and amplifier 32 with pulses from the alpha particle source shown as closely spaced vertical lines which modulate the double sideband, suppressed carrier. FIG. 4 represents the modulated double sideband, suppressed carrier when the system of the invention (which is a closed loop system) is in balance.

Figure 5:
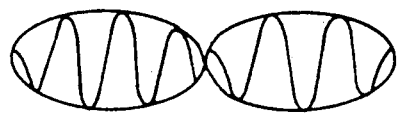
Figure 6:

On line 40 as mentioned above, the output of the detector 33 is in either the waveform shown in FIG. 5 or the waveform shown in FIG. 6 depending upon whether a balanced or out of balance condition, respectively exists. FIG. 5 is for a balanced condition at the operating point 34 of FIG. 2 in which individual pulses have been filtered, with a filter (not shown) having an appropriate time constant leaving a modulated signal. In the balanced condition, the waveform of FIG. 3 is essentially equivalent to the modulated waveform of FIG. 5 in that a zero difference signal is developed between them.

FIG. 6 is for an unbalanced condition when the system in essence operates on the steep portions of the curve in FIG. 2, in a narrow range of the steep portions of the curve straddling the operating point 34. Radioactive pulses in FIG. 6 have also been filtered with a filter having an appropriate time constant, leaving a modulated signal.

Figure 8:
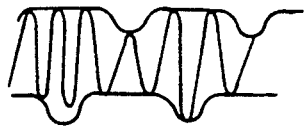

A balanced demodulator 42 inserts a carrier wave, from line 44 and from carrier frequency generator 39, on the signals present on line 40 to bring about signals having the waveforms shown in either FIG. 7 or FIG. 8. FIG. 7 shows the waveform with the carrier frequency added for the balanced condition corresponding to the path distance 28 coinciding with the operating point 34 of FIG. 2. FIG. 8 shows the waveform with the carrier frequency added for the unbalanced condition corresponding to the path distance 28 coinciding with the steep portions of the curve in FIG. 2 above and below the operating point 34.

Figure 9:
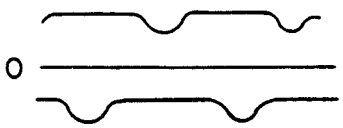

An output from the balanced demodulator 42 representing an unbalanced condition of the alpha particle source 12 is present on line 46 and is shown as the waveform in FIG. 9 where the carrier has been demodulated, and the envelopes are detected. If on the other hand, the signal on line 46 represented a balanced condition of the alpha particle source 12, the waveform would simply be a straight line of zero amplitude (not shown).

Figure 10:
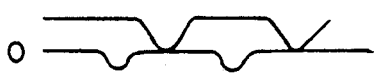

The demodulated envelope signal on line 46 is inputted to D.C. restorer 48 where the signal is clamped to zero to produce, on line 50, the waveform shown in FIG. 10 representing an unbalanced condition. The outputs on line 50 are integrated and filtered in filter 52 to obtain a constant D.C. bipolar error signal on line 54. A positive unbalance condition is shown as the waveform in FIG. 11 which represents a positive error signal. A negative unbalance condition would be depicted by a negative error signal. The constant D.C. bipolar signal on line 54 is fed to the control system 56 which is shown in greater detail in FIG. 13, described below.

From the control system 56, the signal on line 58 drives an analog-to-digital converter 60 which in turn provides a digital signal on line 62. The signal on line 62 serves two purposes. The signal on line 62 drives a digital-to-synchro converter 64, and the signal on line 62 is fed to a read only memory 63 for density readout. The read only memory is previously calibrated using known density sources. The digital-to-synchro converter 64 sends a signal on lines 66 to a control transformer 68. The control transformer 68 also receives double sideband, suppressed carrier signal on line 70 from balanced modulator 35 which serves as a reference signal.

The control transformer 68 includes a three-coil stator 69 which receives digital signals along lines 66 from the digital-to-synchro converter 64. The control transformer 68, movable coil 71, amplifier 45, motor 16, shaft 18, and feedback linkage 15 to the movable coil 71 are standard components in an AC servomechanism for dithering and controlling the alpha particle source 12. More specifically, the feedback linkage 15 is connected to the shaft 18 and turns one way or the other along with the motor 16, whereby the turned linkage 15 turns the movable coil 71 one way or the other to effectively balance out the servomechanism with respect to the reference signal. The amplifier 45 signals the motor 16 when the motor 16 has gone far enough in either direction.

The amplifier 45 receives a reference double sideband, suppressed carrier signal on line 36 from the balanced modulator 35. The amplifier 45 also receives an error signal on line 72 from the control transformer 68. When the reference and error signals on lines 36 and 72, respectively, are equivalent, the servomechanism is quiet, and the motor 16 is not moved. However, when the reference and error signals on lines 36 and 72 are not equivalent, the servomechanism causes the motor 16 to move to reduce the error signal whereby the alpha particle source assembly 12 is caused to dither around the operating point 34.

Figure 12:
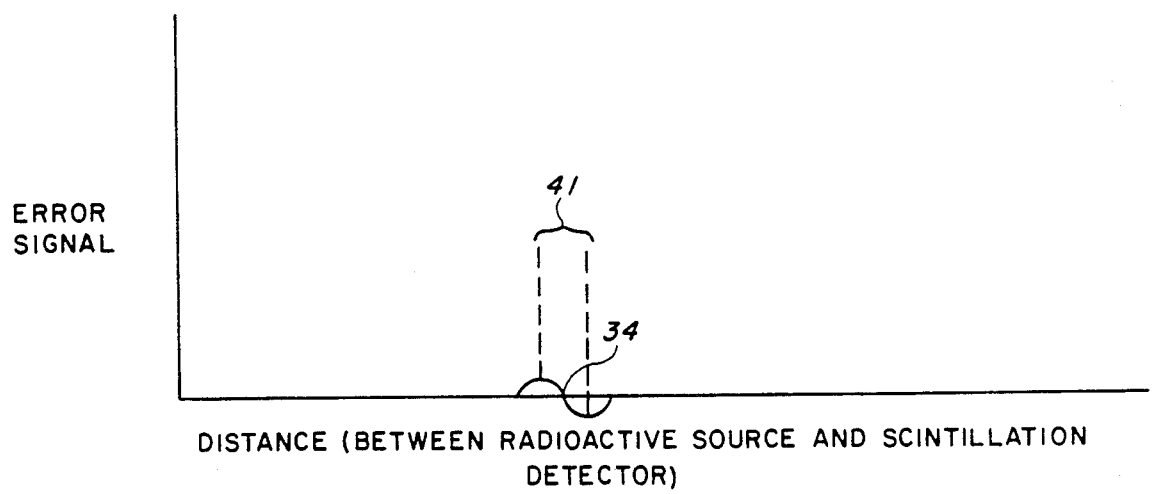
FIG. 12 is a curve showing the relationship of the error signal and the distance between the alpha particle source and the detector assembly.
Figure 11:
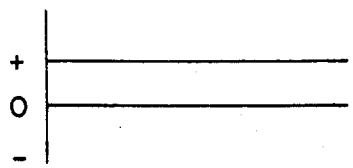

If the alpha particle source assembly 12 would be offset from the steep region of the curve in FIG. 2, an error signal, shown in FIG. 11, would be zero. This condition is shown in FIG. 12 where the error signal is zero for most portions of the curve in FIG. 12, whereby the error signal is zero for most positions of the alpha particle source assembly 12. A zero error signal means that the double sideband, suppressed carrier waveform is not distorted. When, however, the envelope of the double sideband, suppressed carrier signal is distorted within a narrow range straddling, but not at the operating point 34, an error signal is developed. Point 34 in FIG. 12 represents the same operating point 34 in FIG. 2. Region 41 represents the narrow region that straddles the operating point 34. This is the narrow range in which the servomechanism and alpha particle source assembly 12 dither. The positive curve portion in FIG. 12 to the left of operating point 34 represents a positive error signal, and the negative curve portion to the right of operating point 34 represents a negative error signal.

Figure 13:
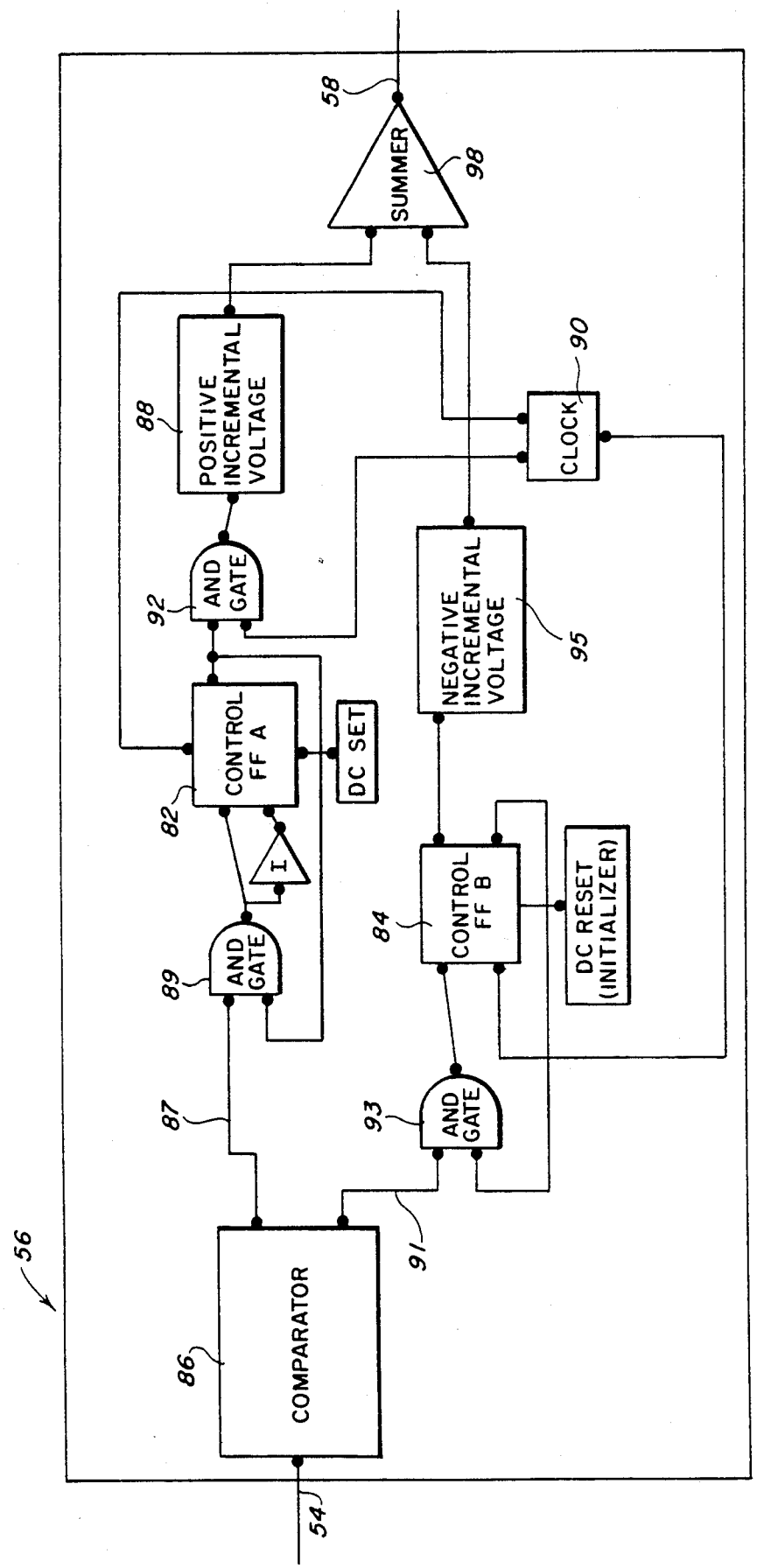
FIG. 13 is a schematic diagram of the control system used to control the motor shown in FIG. 1.

Referring to FIG. 13, the control system shown as element 56 in FIG. 1 is shown in greater detail. In order to operate around the operating point 34 in FIGS. 2 and 12, an incremental and variable voltage is varied in accordance with FIG. 13. When the system is first operated, the path distance 28 is set to a very small distance. Control flip flop 82 is initialized as "set"; and control flip flop 84 is initialized as "reset". The error signal on line 54 is input to comparator 86.

If the error signal is zero or positive, line 87 is energized, AND gate 89 is enabled, and a programmed voltage is incremented by positive incremental voltage source 88 in conjunction with a clock signal from clock 90 by enabling AND gate 92.

When the error signal is negative, line 87 is deenergized, and control flip flop 82 is reset, the AND gate 92 is disabled, and the positive incremental voltage source 88 is no longer incremented. Also, when the error signal is negative, line 91 is energized, AND gate 93 is enabled, flip flop 84 is set, and negative incremental voltage source 95 is activated.

The positive incremental voltage from source 88 and the negative incremental voltage from source 95 are summed in summer 98. The output of summer 98 appears on line 58 (as shown in FIG. 1) and is used to drive the analog-to-digital converter 60 and then the digital-to-synchro converter 64 which in turn drives the control transformer 68, the amplifier 45, and the motor 16, shaft 18, and carriage 14 further in response to the dither signal from the balanced modulator 35.

In FIG. 1, the output signal on line 58, or the digitized output signal on line 62, can be used to determine the density of the medium (e.g. air). More specifically, the density may be read out by means of a read only memory (ROM) 63 based on previously calibrated data.

Numerous benefits are obtained by following the principles of the invention. With the invention, an alpha particle densitometer is provided that automatically compensates for the fact that the alpha particle source undergoes constant decay.

More generally, with the invention, a radioactivity-based densitometer is provided that does not require periodic calibrations due to the decay of the radioactive substance.

With the invention, a very accurate method is provided for measuring the density of air and other low density materials.

It will be understood that various changes in the details, steps and arrangement of parts which have been herein described and illustrated to explain the nature of the invention, may be made by those skilled in the art within the principles and scope of the invention as expressed in the appended claims. For example, instead of the radioactive particle source being dithered by the servomotor, the detector assembly could be dithered instead.

What is claimed is:

1. An apparatus for measuring a characteristic of a medium by measuring radioactive particle absorption in the medium, comprising:
   a radioactive particle source including means for directing radioactive particles from said source into the medium,
   means, spaced from said radioactive particle source by a path distance which traverses a portion of the medium, for detecting the rate of radioactive particle emission which traverses said path distance in the medium, said detecting means providing a radioactive particle detection signal,
   means, responding to said detection signal, for varying said path distance for maintaining a range of predetermined fractions of the rate of emitted radioactive particles that are detected by said detecting means, and means for indicating a characteristic of the medium as a function of said path distance.

2. The apparatus described in claim 1 wherein said path distance is maintained within a range encompassing an operating point which corresponds to the distance at which the detected rate of emitted radioactive particles that have passed through the medium drops rapidly from the rate of radioactive particle emission at said radioactive particle source.

3. The apparatus described in claim 1 wherein said path distance is maintained within a range encompassing an operating point which corresponds to the distance at which the detected rate of emitted radioactive particles that have passed through the medium drops rapidly to approximately one half of the rate of radioactive particle emission from said radioactive particle source.

4. The apparatus described in claim 3 wherein said indicating means comprises means for indicating the density of the medium as a function of said path distance.

5. The apparatus as described in claim 1 wherein said indicating means comprises means for indicating the density of the medium as a function of said path distance.

6. The apparatus described in claim 1 wherein said radioactive particle source emits alpha particles, wherein said detecting means detects alpha particles, and wherein said alpha particle detecting means includes a scintillating substance that responds to alpha particles by emitting scintillations.

7. The apparatus described in claim 1 wherein said means for varying said path distance includes a servomechanism which includes a motor for varying said path distance between said radioactive particle source and said detecting means.

8. The apparatus described in claim 1 for measuring a characteristic of a medium by measuring alpha particle absorption in the medium, wherein said means for varying said path distance includes a double sideband, suppressed carrier signal means for providing a reference signal and an alpha particle modulated signal responsive to said detection signal, means for providing a difference signal representative of a difference between said reference signal and said alpha particle modulated detection signal, said difference signal controlling a servomechanism for controlling said radioactive particle source.

9. The apparatus described in claim 8 wherein said indicating means comprises means for indicating the density of the medium as a function of said path distance, said indicating means including said difference signal providing means.

10. The apparatus described in claim 1, wherein said radioactive particle source is an alpha particle source.

11. The apparatus described in claim 10, wherein said alpha particle source is polonium −210.

12. An apparatus for measuring the density of gaseous medium, comprising:
   an alpha particle source including means for directing the alpha particles to the medium,
   means, spaced from said alpha particle source by a path distance which traverses a portion of the medium, for detecting a range of predetermined fractions of the rate of alpha particle emission from said source, said detecting means providing a detection signal, and
   means, responding to said detection signal, for varying said path distance for maintaining the range of predetermined fractions of the rate of alpha particles detected by said detecting means, and means for indicating density of the medium as a function of said path distance.

13. An apparatus for measuring absorption of radioactivity decay particles in a medium, comprising:
   a source of radioactivity decay particles including means for directing the radioactivity decay particles to the medium,
   means, spaced from said source by a path distance which traverses the medium, for detecting a predetermined fraction of the rate of radioactivity decay particles emitted from said source, said detecting means providing a detection signal, and
   means, responding to said detection signal, for varying said path distance for maintaining the predetermined fraction of the rate of activity decay particles detected by said detecting means, and means for indicating a characteristic of the medium as a function of said path distance.

14. A self-calibrating apparatus for measuring density of air by employing alpha particle absorption, comprising:
   an alpha particle source including means for directing the alpha particles to the air whose density is being measured,
   means, spaced from said alpha particle source by a path distance which traverses a portion of the air, for detecting approximately one half of the rate of alpha particle emission from said source, said detecting means providing a detection signal,
   double sideband, suppressed carrier means for providing a reference signal and a modulated signal responsive to said detection signal,
   means for providing a difference signal representative of a difference between said reference signal and said modulated detection signal, and
   means for moving said alpha particle source for automatically varying said path distance for maintaining the rate of alpha particle emission detected by said detecting means at approximately one half the rate emitted from said source, said moving means being responsive to said difference signal, the variation of said path distance being representative of the density of the air.

15. A method for measuring absorption of radioactivity decay particles in a medium, comprising the steps of:
   obtaining a source of radioactivity decay particles and directing the particles to the medium, spacing a detector from the source by a path distance which traverses a portion of the medium, detecting a predetermined fraction of the rate of particles emitted from the radioactive source by a detector and providing a detection signal, and responding to the detection signal by varying the path distance for maintaining the predetermined fraction of the rate of radioactive particles detected by the detector in a manner effective to cause variation of the path distance to be indicative of variation in particle absorption characteristics of the medium.

16. A method for measuring density of air by employing alpha particle absorption, comprising the steps of:

obtaining an alpha particle source, detecting approximately one half of the rate of alpha particle emission form the source in a manner effective to cause a detection signal to be provided, employing a double sideband, suppressed carrier to provide a reference signal and to provide a signal representing modulation of the double sideband, suppressed carrier by the detection signal, obtaining a difference signal representative of a difference between the reference signal and the modulated detection signal, and utilizing the difference signal for operating a feedback controlled servomechanism for moving the alpha particle source for automatically maintaining the rate of alpha particle emission detected at approximately one half the rate of alpha particle emission, wherein the moving of the alpha particle source is done in a manner effective to indicate variation in the density of the air and to cause the alpha particle source to be self-calibrated.

* * * * *